United States Patent
Onuma et al.

(10) Patent No.: US 8,597,258 B2
(45) Date of Patent: Dec. 3, 2013

(54) VALVED CATHETER

(75) Inventors: Tadatsugu Onuma, Fukuroi (JP); Masanori Makino, Fukuroi (JP); Emiyo Sonoyama, Fukuroi (JP)

(73) Assignee: Covidien LP, Mansfield, MA (US)

( * ) Notice: Subject to any disclaimer, the term of this patent is extended or adjusted under 35 U.S.C. 154(b) by 310 days.

(21) Appl. No.: 12/869,817

(22) Filed: Aug. 27, 2010

(65) Prior Publication Data

US 2011/0054415 A1    Mar. 3, 2011

(30) Foreign Application Priority Data

Aug. 31, 2009  (JP) ................ 2009-199639

(51) Int. Cl.
*A61M 5/00*     (2006.01)
(52) U.S. Cl.
USPC ..................... 604/247; 604/246; 604/264
(58) Field of Classification Search
USPC ................. 604/264, 266, 523, 246, 247
See application file for complete search history.

(56) References Cited

U.S. PATENT DOCUMENTS

| | | | |
|---|---|---|---|
| 4,391,276 A | 7/1983 | Lazarus et al. | |
| 4,403,983 A | 9/1983 | Edelman et al. | |
| 4,475,898 A | 10/1984 | Brodner et al. | |
| 4,493,696 A | 1/1985 | Uldall | |
| 4,549,879 A | 10/1985 | Groshong et al. | |
| 4,568,329 A | 2/1986 | Mahurkar | |
| 4,583,968 A | 4/1986 | Mahurkar | |
| 4,619,643 A | 10/1986 | Bai | |
| 4,626,240 A | 12/1986 | Edelman et al. | |
| 4,643,711 A | 2/1987 | Bates | |
| 4,671,796 A | 6/1987 | Groshong et al. | |
| 4,692,141 A | 9/1987 | Mahurkar | |

(Continued)

FOREIGN PATENT DOCUMENTS

| | | |
|---|---|---|
| EP | 0 299 622 A2 | 1/1989 |
| EP | 0 299 622 A3 | 1/1989 |

(Continued)

OTHER PUBLICATIONS

European Search Report issued by European Patent Office in EP Application No. EP 09 25 1289, completed Sep. 22, 2009 (6 pages).

(Continued)

*Primary Examiner* — Nicholas Lucchesi
*Assistant Examiner* — Leah Stohr
(74) *Attorney, Agent, or Firm* — John Paul Mello, Esq (57) ABSTRACT

A valved catheter is provided which includes a slit that opens readily in both directions either when a fluid is caused to flow from the interior to the exterior thereof or when a fluid is caused to flow from the exterior to the interior thereof, and that prevents inadvertent closure thereof from the opened state. The valve includes an openable slit that penetrates from the inner surface to the outer surface of a distal end section of a valved catheter with a closed distal end, and edge portions on the two sides of the slit are formed along the direction in which the valved catheter extends. The slit includes a linear shape in the cross-section of the distal end section of the valved catheter that extends in a position away from a center line "c" that passes through the center of the valved catheter in parallel with this center line "c" whereupon, either one of the edge portions deforms more readily than either one of the other edge portions.

7 Claims, 5 Drawing Sheets

(56) References Cited

U.S. PATENT DOCUMENTS

| | | |
|---|---|---|
| 4,701,166 A | 10/1987 | Groshong et al. |
| 4,753,640 A | 6/1988 | Nichols et al. |
| 4,769,005 A | 9/1988 | Ginsburg et al. |
| 4,772,268 A | 9/1988 | Bates |
| 4,772,269 A | 9/1988 | Twardowski et al. |
| 4,795,439 A | 1/1989 | Guest |
| 4,808,155 A | 2/1989 | Mahurkar |
| 4,808,156 A | 2/1989 | Dean |
| 4,813,934 A | 3/1989 | Engelson et al. |
| 4,842,582 A | 6/1989 | Mahurkar |
| 4,895,561 A | 1/1990 | Mahurkar |
| 4,897,079 A | 1/1990 | Zaleski et al. |
| 4,961,809 A | 10/1990 | Martin |
| 4,973,319 A | 11/1990 | Melsky |
| 4,995,863 A * | 2/1991 | Nichols et al. ............ 604/247 |
| 4,995,865 A | 2/1991 | Gahara et al. |
| 5,009,636 A | 4/1991 | Wortley et al. |
| 5,035,399 A | 7/1991 | Rantanen-Lee |
| 5,041,083 A | 8/1991 | Tsuchida et al. |
| 5,053,004 A | 10/1991 | Market et al. |
| 5,053,023 A | 10/1991 | Martin |
| 5,057,073 A | 10/1991 | Martin |
| 5,059,170 A | 10/1991 | Cameron |
| 5,085,632 A | 2/1992 | Ikada et al. |
| 5,106,368 A | 4/1992 | Uldall et al. |
| 5,112,301 A | 5/1992 | Fenton, Jr. et al. |
| 5,135,599 A | 8/1992 | Martin et al. |
| 5,147,332 A | 9/1992 | Moorehead |
| 5,156,592 A | 10/1992 | Martin et al. |
| 5,160,325 A | 11/1992 | Nichols et al. |
| 5,167,623 A | 12/1992 | Cianci et al. |
| 5,171,218 A | 12/1992 | Fonger et al. |
| 5,188,593 A | 2/1993 | Martin |
| 5,190,520 A | 3/1993 | Fenton, Jr. et al. |
| 5,195,962 A | 3/1993 | Martin et al. |
| 5,197,951 A | 3/1993 | Mahurkar |
| 5,209,723 A | 5/1993 | Twardowski et al. |
| 5,219,335 A | 6/1993 | Willard et al. |
| 5,221,255 A | 6/1993 | Mahurkar et al. |
| 5,221,256 A | 6/1993 | Mahurkar |
| 5,224,938 A | 7/1993 | Fenton, Jr. |
| 5,250,034 A | 10/1993 | Appling et al. |
| 5,261,885 A | 11/1993 | Lui |
| 5,267,979 A | 12/1993 | Appling et al. |
| 5,304,155 A | 4/1994 | Lui |
| 5,308,338 A | 5/1994 | Helfrich |
| 5,346,471 A | 9/1994 | Raulerson |
| 5,348,536 A | 9/1994 | Young et al. |
| 5,360,397 A | 11/1994 | Pinchuk |
| 5,364,344 A | 11/1994 | Beattie et al. |
| 5,374,245 A | 12/1994 | Mahurkar |
| 5,378,230 A | 1/1995 | Mahurkar |
| 5,380,276 A | 1/1995 | Miller et al. |
| 5,395,316 A | 3/1995 | Martin |
| 5,403,291 A | 4/1995 | Abrahamson |
| 5,405,341 A | 4/1995 | Martin |
| 5,451,206 A | 9/1995 | Young |
| 5,464,398 A | 11/1995 | Haindl |
| 5,472,417 A | 12/1995 | Martin et al. |
| 5,480,380 A | 1/1996 | Martin |
| 5,486,159 A | 1/1996 | Mahurkar |
| 5,489,278 A | 2/1996 | Abrahamson |
| 5,509,897 A | 4/1996 | Twardowski et al. |
| 5,522,807 A | 6/1996 | Luther |
| 5,531,679 A | 7/1996 | Schulman et al. |
| 5,554,136 A | 9/1996 | Luther |
| 5,556,390 A | 9/1996 | Hicks |
| 5,569,182 A | 10/1996 | Twardowski et al. |
| 5,571,093 A | 11/1996 | Cruz et al. |
| D381,420 S | 7/1997 | Musgrave et al. |
| D384,411 S | 9/1997 | Musgrave et al. |
| D384,741 S | 10/1997 | Musgrave et al. |
| 5,683,640 A | 11/1997 | Miller et al. |
| 5,685,867 A | 11/1997 | Twardowski et al. |
| 5,702,365 A | 12/1997 | King |
| 5,718,678 A | 2/1998 | Fleming, III |
| 5,776,096 A | 7/1998 | Fields |
| 5,797,869 A | 8/1998 | Martin et al. |
| 5,807,311 A | 9/1998 | Palestrant |
| 5,807,329 A | 9/1998 | Gelman |
| 5,807,349 A | 9/1998 | Person et al. |
| 5,810,789 A | 9/1998 | Powers et al. |
| 5,830,184 A | 11/1998 | Basta |
| 5,830,196 A | 11/1998 | Hicks |
| 5,868,717 A | 2/1999 | Prosl |
| 5,928,203 A | 7/1999 | Davey et al. |
| 5,947,953 A | 9/1999 | Ash et al. |
| 5,961,485 A | 10/1999 | Martin |
| 5,961,486 A | 10/1999 | Twardowski et al. |
| 5,968,009 A | 10/1999 | Siman |
| 5,976,103 A | 11/1999 | Martin |
| 5,984,903 A | 11/1999 | Nadal |
| 5,989,206 A | 11/1999 | Prosl et al. |
| 5,989,213 A | 11/1999 | Maginot |
| 5,993,437 A | 11/1999 | Raoz |
| 6,001,079 A | 12/1999 | Pourchez |
| 6,004,310 A | 12/1999 | Bardsley et al. |
| 6,099,519 A | 8/2000 | Olsen et al. |
| 6,123,725 A | 9/2000 | Aboul-Hosn |
| 6,126,631 A | 10/2000 | Loggie |
| 6,146,354 A | 11/2000 | Beil |
| 6,156,016 A | 12/2000 | Maginot |
| 6,190,349 B1 | 2/2001 | Ash et al. |
| 6,190,371 B1 | 2/2001 | Maginot et al. |
| 6,206,849 B1 | 3/2001 | Martin et al. |
| 6,273,875 B1 | 8/2001 | Siman et al. |
| 6,280,423 B1 | 8/2001 | Davey et al. |
| 6,293,927 B1 | 9/2001 | McGuckin, Jr. |
| 6,342,120 B1 | 1/2002 | Basta |
| 6,346,090 B1 | 2/2002 | Liska et al. |
| 6,394,141 B2 | 5/2002 | Wages et al. |
| 6,409,700 B1 | 6/2002 | Siegel, Jr. et al. |
| 6,447,488 B2 | 9/2002 | Estabrook et al. |
| 6,461,321 B1 | 10/2002 | Quinn |
| 6,475,207 B1 | 11/2002 | Maginot et al. |
| 6,482,169 B1 | 11/2002 | Kuhle |
| 6,506,182 B2 | 1/2003 | Estabrook et al. |
| 6,579,261 B1 | 6/2003 | Kawamura |
| 6,585,705 B1 | 7/2003 | Maginot et al. |
| 6,592,542 B2 | 7/2003 | Childers et al. |
| 6,592,558 B2 | 7/2003 | Quah |
| 6,595,966 B2 | 7/2003 | Davey et al. |
| 6,620,118 B1 | 9/2003 | Prosl et al. |
| 6,638,242 B2 | 10/2003 | Wilson et al. |
| 6,692,473 B2 | 2/2004 | St. Cyr et al. |
| 6,695,832 B2 | 2/2004 | Schon et al. |
| 6,719,749 B1 | 4/2004 | Schweikert et al. |
| 6,723,084 B1 | 4/2004 | Maginot et al. |
| 6,730,096 B2 | 5/2004 | Basta |
| 6,743,218 B2 | 6/2004 | Maginot et al. |
| 6,749,580 B2 | 6/2004 | Work et al. |
| 6,758,836 B2 | 7/2004 | Zawacki |
| 6,786,884 B1 | 9/2004 | DeCant, Jr. et al. |
| 6,808,510 B1 | 10/2004 | DiFiore |
| 6,814,718 B2 | 11/2004 | McGuckin, Jr. et al. |
| 6,858,019 B2 | 2/2005 | McGuckin, Jr. et al. |
| 6,921,396 B1 | 7/2005 | Wilson et al. |
| 6,942,635 B2 | 9/2005 | Rosenblatt et al. |
| 6,942,653 B2 | 9/2005 | Quinn |
| 6,966,886 B2 | 11/2005 | Appling |
| 6,969,381 B2 | 11/2005 | Voorhees |
| 6,976,973 B1 | 12/2005 | Ruddell et al. |
| 6,986,752 B2 | 1/2006 | McGuckin, Jr. et al. |
| 6,991,625 B1 | 1/2006 | Gately et al. |
| 7,008,395 B1 | 3/2006 | Loggie |
| 7,008,412 B2 | 3/2006 | Maginot |
| 7,011,645 B2 | 3/2006 | McGuckin, Jr. et al. |
| 7,013,928 B2 | 3/2006 | Navis |
| 7,048,680 B2 | 5/2006 | Viole et al. |
| 7,066,914 B2 | 6/2006 | Andersen |
| 7,077,829 B2 | 7/2006 | McGuckin, Jr. et al. |
| 7,413,564 B2 | 8/2008 | Morris et al. |
| 2002/0121282 A1 | 9/2002 | McGuckin, Jr. et al. |
| 2002/0156430 A1 * | 10/2002 | Haarala et al. ............ 604/247 |

(56) References Cited

U.S. PATENT DOCUMENTS

| | | |
|---|---|---|
| 2002/0156460 A1 | 10/2002 | Ye et al. |
| 2003/0032918 A1 | 2/2003 | Quinn |
| 2003/0093029 A1 | 5/2003 | McGuckin, Jr. et al. |
| 2003/0191425 A1 | 10/2003 | Rosenblatt et al. |
| 2004/0176743 A1 | 9/2004 | Morris et al. |
| 2004/0249337 A1 | 12/2004 | DiFiore |
| 2005/0033222 A1 | 2/2005 | Haggstrom et al. |
| 2005/0085765 A1 | 4/2005 | Voorhees |
| 2005/0090776 A1 | 4/2005 | McGuckin et al. |
| 2005/0215978 A1 | 9/2005 | Ash |
| 2005/0228339 A1 | 10/2005 | Clark |
| 2005/0267400 A1 | 12/2005 | Haarala et al. |
| 2005/0288623 A1 | 12/2005 | Hjalmarsson |
| 2006/0004325 A1 | 1/2006 | Hamatake et al. |
| 2006/0149191 A1 | 7/2006 | DiFiore |
| 2006/0253063 A1 | 11/2006 | Schweikert |
| 2007/0100298 A1 | 5/2007 | Appling |
| 2009/0054825 A1 | 2/2009 | Melsheimer et al. |
| 2009/0312718 A1 | 12/2009 | Onuma |
| 2010/0069818 A1 | 3/2010 | Smouse |
| 2010/0081986 A1 | 4/2010 | Matson |
| 2011/0130745 A1 | 6/2011 | Shevgoor et al. |

FOREIGN PATENT DOCUMENTS

| | | |
|---|---|---|
| EP | 0 554 722 A1 | 8/1993 |
| EP | 0 322 225 B1 | 2/1995 |
| EP | 0 713 406 B1 | 3/1998 |
| EP | 0 864 336 A2 | 9/1998 |
| EP | O864 336 A3 | 3/1999 |
| EP | 0 570 530 BI | 8/1999 |
| EP | 0 555 780 B1 | 9/1999 |
| EP | 1 595 565 A1 | 11/2005 |
| EP | I144 039 B1 | 12/2005 |
| EP | 2 168 625 | 3/2010 |
| JP | 63-84243 | 6/1988 |
| JP | 2571353 | 1/1997 |
| JP | 2007-175297 A | 7/2007 |
| WO | WO 95/04567 | 2/1995 |
| WO | WO 97/37699 A1 | 10/1997 |
| WO | WO 98/41277 | 9/1998 |
| WO | WO 99/38550 | 8/1999 |
| WO | WO 99/65557 | 12/1999 |
| WO | WO 00/06239 A2 | 2/2000 |
| WO | WO 01/91845 A1 | 12/2001 |
| WO | WO 02/13899 A1 | 2/2002 |
| WO | WO 02/18004 A3 | 3/2002 |
| WO | WO 03/033049 A3 | 4/2003 |
| WO | WO 03/066148 A1 | 8/2003 |
| WO | WO 2004/093956 A1 | 11/2004 |
| WO | WO 2005/023336 A2 | 3/2005 |
| WO | WO 2005/077449 A1 | 8/2005 |
| WO | WO 2005/084741 A1 | 9/2005 |
| WO | WO 2006/014339 A2 | 2/2006 |

OTHER PUBLICATIONS

Extended European Search Report corresponding to EP Application No. 09 17 0662. completed Jan. 11, 2010; mailed Jan. 27, 2010 (7 pages).

EP Search Report from EP Application No. EP 12 18 4656 dated May 11, 2012.

Official Action mailed Jul. 23, 2013 in counterpart Japanese Appl. No. 2009-199639. (6 pgs. with English translation).

\* cited by examiner

VALVED CATHETER

CROSS-REFERENCE TO RELATED APPLICATIONS

This application claims priority under 35 U.S.C. §119 to Japanese Patent Application Serial No. 2009-199639, filed Aug. 31, 2009, the entire contents of which are incorporated by reference in their entirety.

TECHNICAL FIELD

The present disclosure relates to a valved catheter through which a fluid is able to pass from the interior to the exterior thereof, and from the exterior to the interior thereof, by way of a valve including a slit.

DESCRIPTION OF RELATED ART

The temporary and long-term delivery of medical fluids, including anti-cancer agents and nutrients, into the vein of a patient conventionally involves, for example, the placement of a catheter in the body of the patient. Stable injection of medical fluids employing such catheters necessitates the avoidance of catheter blockage while the medical fluid is being injected. However, when catheters with an open distal end are employed, blood is able to infiltrate into the catheter where it coagulates and causes the blockage thereof. While catheter blockage by blood is commonly prevented by filling the lumen of the catheter with a heparin-added physiological saline solution or the like, this renders the operation pertaining to the placement of the catheter in the body of the patient more troublesome and, moreover, increases the burden on the medical practitioner and the patient.

To that end, a valved catheter that prevents catheter blockage caused by coagulated blood using a design based on the elimination of the opened distal end and the provision of a valve that is normally closed and opens only when a medical fluid or blood is being extracted between the interior and the exterior of the catheter has been developed (see, for example, U.S. Pat. No. 7,413,564). In this slit valve catheter (valved catheter), an elongate recessed portion is formed along the longitudinal direction thereof, and a slit is formed in the center of this recessed portion along the longitudinal direction of the recessed portion.

The slit of this slit valve catheter is designed to open both inward and outward by a comparatively small pressure and, when a predetermined pressure differential is generated between the interior and exterior of the slit valve catheter, the slit valve opens to facilitate either the injection of a medical fluid into a vein or the extraction of blood from a vein through the catheter. In addition, this slit is closed in the absence of the generation of this predetermined pressure differential between the interior and exterior of the slit valve catheter and, accordingly, blood coagulation within the slit is prevented.

However, in the conventional valved catheter described above, the opposing surfaces of the edge portions of the two sides of the slit of the valve catheter are in intimate contact, and simultaneously deform while retaining their symmetrical shape when the slit opens and closes. For this reason, the slit is less readily able to be opened from the closed state at low fluid pressure due to the pressure contact between these opposing surfaces, and is less readily able to be closed from the opened state.

SUMMARY

With the foregoing conditions in mind, it is an object of the present disclosure to provide a valved catheter that includes a slit that opens readily in both directions when either a fluid is caused to flow from the interior to the exterior thereof or when a fluid is caused to flow from the exterior to the interior thereof, and that prevents inadvertent closure thereof from the opened state.

A characterizing feature of the constitution of the valved catheter pertaining to the present disclosure for achieving this object resides in a resilient and flexible valved catheter which is made from a resin and which is formed in a tube shape with a closed distal end and in which a valve including an openable slit that penetrates from the inner surface to the outer surface is formed along the longitudinal direction in this distal end section, a first edge portion of the edge portions of the two sides of the slit of the valve being deformed more readily than the other edge portion when either a fluid is caused to flow from the interior to the exterior by way of the valve, or when a fluid is caused to flow from the exterior to the interior by way of the valve.

In the valved catheter of the present disclosure of the constitution described above, a first edge portion of the edge portions of the two sides of the slit of the valve including a slit is deformed more readily by the pressure of a fluid than the other edge portion. Accordingly, the two edge portions of the slit do not deform simultaneously and, instead, the slit is opened slightly due to the initial deformation of the first edge portion, and is subsequently opened sufficiently to allow fluid to pass therethrough due to the force that is generated by the flow of fluid. In addition, even if the other edge portion is deformed in a direction for closing the slit from the opened slit state, because the first edge portion does not deform simultaneously with the other edge portion and a state that allows the flow of fluid to occur is able to be maintained, the slit closes gradually as the fluid pressure drops and as the first edge portion approaches the other edge portion.

In this case, the first edge portion that deforms more readily and the other edge portion that deforms less readily than the first edge portion are interchangeable in accordance with whether the fluid is passing from the interior to the exterior of the circular tube-shaped body or if the fluid is passing from the exterior to the interior of the circular tube-shaped body. Accordingly, the slit opens readily not only when fluid flows from the interior to the exterior of the valved catheter but also when fluid flows from the exterior to the interior of the valved catheter and, as a result, the bi-directional inward and outward flow of fluid therethrough is able to be effected smoothly. In addition, when little or no pressure differential exists between the interior and the exterior of the valved catheter, the closed state of the slit is maintained.

Notably, the term fluid referred to in the present disclosure describes fluids that are injected into the vein of a patient such as medical fluids, including anti-cancer agents and nutrients, and fluids that are extracted from the vein, including blood. The fluid that flows from the interior to the exterior of the valved catheter shall be hereinafter referred to as a medical fluid, while the fluid that flows from the exterior to the interior of the valved catheter shall be hereinafter referred to as blood. In addition, the cross-sectional shape of the tube-shaped valved catheter may be circular or elliptical, or a range of shapes similar thereto.

Another characterizing feature of the valved catheter pertaining to the present disclosure resides in the shape of the adjoining sections of the slit in the cross-section orthogonal to the longitudinal direction of the distal end section of the valved catheter being described by the asymmetry of the edge portions of the two sides about the slit.

The asymmetry of the edge portions of the two sides about the slit described herein refers to a relationship whereby, bending the cross-sectional shape of the valved catheter about the slit, the adjoining sections to the two edge portions of the slit do not overlap perfectly. For example, for a valved catheter of a circular cross-sectional shape, the slit describes a linear shape in the cross-section of the valved catheter, and is located in a position away from an imaginary straight line (where it does not overlap this imaginary straight line) passing through the center of the valved catheter. In addition, for a valved catheter of an elliptical cross-sectional shape, the slit describes a linear shape in the cross-section of the valved catheter, and is located in a position away from the directions in which the long axis and short axis thereof passing through the center of the valved catheter extend.

Accordingly, because the shape of the adjoining sections to the edge portions of the two sides of the slit is always asymmetrical about the slit, either one of the edge portions is able to be more readily deformed than the other edge portion by the pressure exerted thereon by the medical fluid. In addition, once the slit is open, the slit does not close until the fluid pressure drops and the more readily deformable edge portion approaches the other edge portion and, accordingly, the slit closes gradually and the inadvertent closure thereof is prevented.

A further characterizing feature of the valved catheter pertaining to the present disclosure resides in the valved catheter being formed in a tube shape with a circular cross-section, the slit describing a linear shape in the cross-section in a position away from an imaginary straight line passing through the center of the valved catheter and extending in parallel with the imaginary straight line and, taking a minimum distance from the imaginary straight line to the slit as "a," and a distance equivalent to "a" subtracted from ½ of the inner diameter of the circular tube-shaped shaped body as "b," "a" being greater than "b."

Accordingly, when a medical fluid is caused to flow from the interior to the exterior of the valved catheter, the slit opens readily as a result of the pressure exerted thereon by the medical fluid in such a way that the edge portion of the edge portions of the two sides of the slit of the side away from the imaginary straight line separates outward with respect to the edge portion on the imaginary straight line side. In addition, when blood flows from the exterior to the interior of the valved catheter, the slit opens readily as a result of the pressure that is exerted thereof by the blood in such a way that the edge portion of the edge portions of the two sides of the slit of the imaginary straight line side separates inwardly with respect to the edge portion of the side away from the imaginary straight line. In addition, once the slit is open, because the slit does not close until the fluid pressure drops and the more readily deformable edge portion approaches the other edge portion, the slit closes gradually and the inadvertent closure thereof is able to be prevented. Furthermore, the valved catheter produced in accordance with the present disclosure is ideal in terms of the suitability of the ease of opening thereof, and in being able to close gradually in response to the drop in fluid pressure when closing from an opened state.

Another characterizing feature of the constitution of the valved catheter of the present disclosure resides in the edge portions of the two sides of the slit of the valve being constituted by resins of different hardness.

Accordingly, because the hardness of the first edge portion of the edge portions of the two sides of the slit is less than the hardness of the other edge portion, the first edge portion of the slit is more readily deformable than the other edge portion. For this reason, when a medical fluid flows from the interior to the exterior of the valved catheter, the slit opens readily due to the pressure that is exerted thereon by the medical fluid in such a way that the first edge portion of the two edge portions of the slit separates outwardly with respect to the other edge portion, and when blood flows from the exterior to the interior of the valved catheter, the slit opens readily due to the pressure that is exerted thereon by the blood in such a way that the first edge portion of the two edge portions of the slit separates inwardly with respect to the other edge portion. That is to say, the slit opens readily when either a medical fluid is caused to flow from the interior to the exterior of the valved catheter or when blood is caused to flow from the exterior to the interior thereof, and inadvertent closure from the opened state thereof is prevented. The resins employed in this case may be resins of different types, or they may be identical resins of different hardness.

An additional characterizing feature of the constitution of the valved catheter pertaining to the present disclosure resides in a contrast-imparting material of greater hardness than the resin being incorporated into the other edge portion of the slit of the valve.

Accordingly, when the valved catheter is positioned within the body, the slit is able to be readily opened using the contrast-imparting material thereof as a means for confirming the position of the valved catheter. That is to say, because the contrast-imparting material is normally constituted of barium or tungsten which is harder than the resin, the incorporation of this contrast-imparting material in the other edge portion of the slit ensures that the hardness of the other edge portion is greater than the hardness of the first edge portion of this slit. As a result, when either a medical fluid is caused to flow from the interior to the exterior of the valved catheter or when blood is caused to flow from the exterior to the interior, the slit is able to be more readily opened, and inadvertent closure from the opened state is able to be prevented. In this case, the contrast-imparting material may be incorporated in the other edge portion as a powder, or it may be incorporated in the other edge portion as fibers.

An additional characterizing feature of the constitution of the valved catheter pertaining to the present disclosure resides in the thickness of the first edge portion of the slit of the valve being thinner than the other edge portion. Accordingly, when either a medical fluid is caused to flow from the interior to the exterior of the valved catheter or when blood is caused to flow from the exterior to the interior of the valved catheter, the slit is able to be more readily opened, and inadvertent closure thereof from the opened state is able to be prevented.

BRIEF DESCRIPTION OF THE DRAWINGS

FIGS. 1A-1B show a valved catheter of a first embodiment of the present disclosure of which.

FIGS. 4A-4B show a distal end section of a valved catheter of a second embodiment of the present disclosure of which.

FIGS. 6A-6B show a distal end section of a valved catheter of a third embodiment of the present disclosure of which.

DESCRIPTION OF THE EMBODIMENTS

Figure 1A:
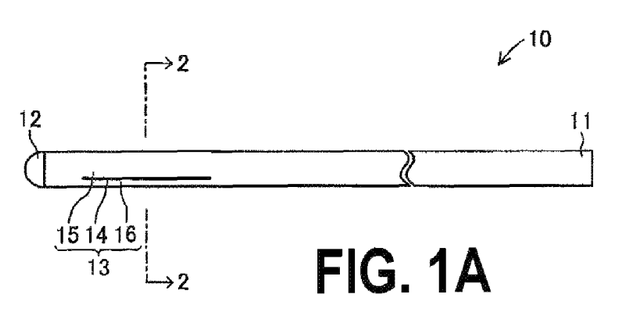
FIG. 1A is a side view and FIG. 1B is a rear view thereof.
Figure 1B:
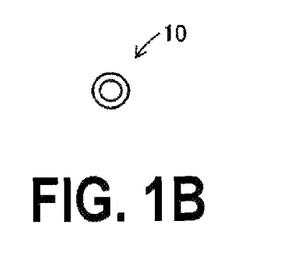
Figure 2:
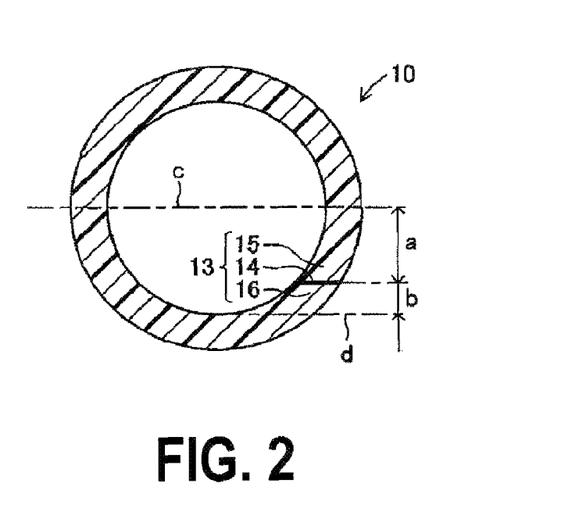
FIG. 2 is a cross-sectional view taken along the line 2-2 of FIG. 1A.
Figure 3:
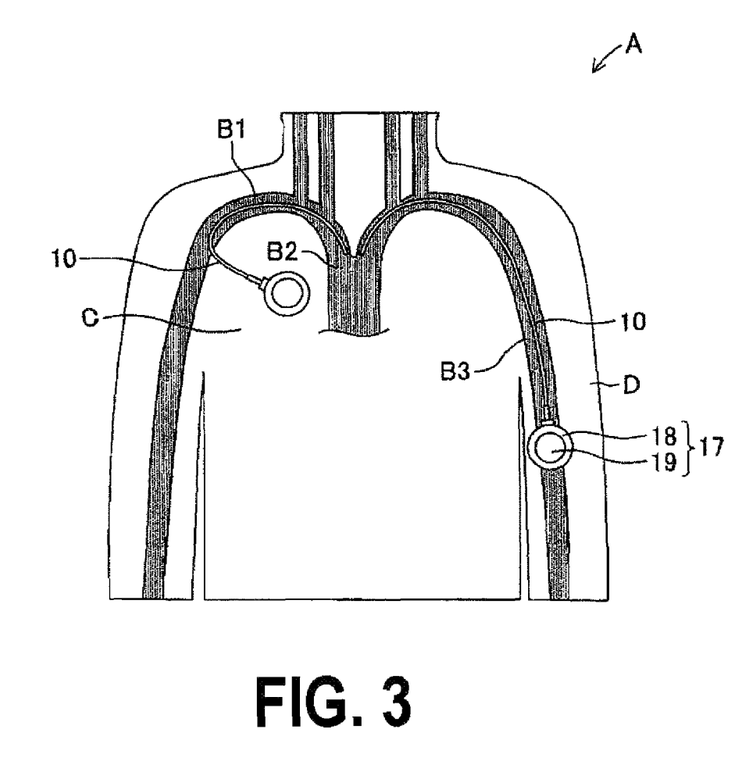
FIG. 3 is an explanatory diagram of the valved catheter when placed in the body of a patient.

A first embodiment of the valved catheter pertaining to the present disclosure will be hereinafter described in detail with reference to the drawings. FIGS. 1A-1B and FIG. 2 show a valved catheter 10 of this embodiment. The valved catheter 10, which is used for delivering a medical fluid such as an anticancer agent or nutrients into a vein (reference characters B1 to B3 and so on as shown in FIG. 3) of a patient A, is placed in the patient A by the connection of a port 17 to a proximal end portion 11 thereof. The valved catheter 10, which is constituted by an elongate, circular tube-shaped body composed of a soft polyurethane resin, is resilient and flexible.

In addition, a dome-shaped wall portion 12 is formed in the distal end of the valved catheter 10, and the distal end of the valved catheter 10 is closed by this wall portion 12. The wall portion 12, which is composed of silicon or polyurethane that is softer than the main body of the valved catheter 10, is fastened to the main body of the valved catheter 10 by adhesion or fusion. An elongate valve 13 that extends along the axial direction (longitudinal direction) of the valved catheter 10 is formed in a section of the circumferential surface portion of the valved catheter 10 more towards the proximal end portion 11 side than the wall portion 12.

The valve 13 is constituted by a linear slit 14 that extends along the axial direction of the valved catheter 10, and by edge portions 15, 16 formed in the two sides of the slit 14 (two sides around the circumference thereof). The slit 14 penetrates from the inner circumferential surface to the outer circumferential surface of the valved catheter 10 and, as shown in FIG. 2, is formed in parallel with an imaginary straight line drawn as the center line "c" of the present disclosure. In addition, taking a tangent line that touches the inner circumferential surface of the valved catheter 10 and that runs parallel to the center line "c" as "d," a length "a" from the center line "c" to the slit 14 is set longer than a length "b" from the tangent line "d" to the slit 14. In this case, the length of "a" is set so as to be approximately twice the length of the length "b." The edge portion 15 is constituted by the adjoining section of the edge portion on the center line "c" side of the slit 14, and the edge portion 16 is constituted by the adjoining section of the edge portion on the tangent line "d" side of the slit 14.

The slit 14 opens as a result of the deformation of the edge portions 15, 16 when the pressure exerted orthogonally on the inner surface and the outer surface of the valve 13 reaches, for example, at least 50 to 60 cm $H_2O$. In this case, when a positive pressure is exerted on the inner surface of the valved catheter 10 and a negative pressure is exerted on its outer surface, the slit 14 opens initially as a result of the edge portion 16 being pressured outwardly away from the edge portion 15. In addition, when a positive pressure is exerted on the outer surface of the valved catheter 10 and a negative pressure is exerted on its inner surface, the slit 14 opens as a result of the edge portion 15 being pressured inwardly away from the edge portion 16. In the absence of any pressure being exerted on the valve 13, or when the pressure exerted thereon is less than a predetermined value, the resilience of the valve 13 ensures intimate contact between the opposing surfaces of the edge portions 15, 16 from which the slit 14 is formed and, accordingly, ensures closure of the slit 14.

When the valved catheter 10 of this constitution is employed to deliver a medical fluid into the vein of a patient A, the port 17 is initially connected to the proximal end portion 11 of the valved catheter 10. The port 17, which is constituted by fastening a septum 19 to the upper surface of a circular plate-shaped main body 18, includes a space portion (not shown in the drawing) formed in its interior. The septum 19 is constituted of a material through which a needle is able to be inserted that possesses a property whereby, upon removal of the needle, the hole created by the insertion of the needle closes up. Accordingly, when the needle of a syringe filled with a medical fluid is inserted in the septum 19 of the port 17 and a medical fluid is injected through the syringe into the port 17, the medical fluid is able to pass from the space portion of the port 17 through the interior of the valved catheter 10 and flow outwardly therefrom through the slit 14.

As shown in FIG. 3, the valved catheter 10 to which the port 17 is connected is able to be inserted through a chest portion C of the patient A into a vein, or is able to be inserted through an arm portion D of the patient A into a vein. When the valved catheter 10 to which the port 17 is connected is to be inserted through the chest portion C into the vein, an incision is made in the adjoining section of a vein of the chest portion C such as, for example, the subclavian vein B1, whereupon the valved catheter 10 is inserted through the subclavian vein B1 located in proximity to this section, and the distal end section thereof is then passed through to a superior caval vein B2. The port 17 is then subcutaneously embedded in the chest portion.

In addition, when the valved catheter 10 to which the port 17 is connected is to be inserted through the arm portion D into the vein, an incision is made in the upper arm section of the arm portion D, whereupon the valved catheter 10 is inserted through a brachial vein B3 located in proximity thereto and its distal end section is then passed from the brachial vein B1 through to the superior caval vein B2. The port 17 is then subcutaneously embedded in the chest portion. In both cases, a state in which the interior portion between the valved catheter 10 and the port 17 is filled with a physiological saline solution is established. Accordingly, the inward pressure of the valved catheter 10 is essentially the same as the outward pressure thereof and, as a result, the closed state of the slit 14 is able to be maintained.

When a medical fluid is to be delivered to the vein of the patient A by way of the valved catheter 10 to which the port 17 is connected, the needle of the syringe filled with the medical fluid is first inserted through the surface of the skin and passed through the septum 19, and the tip of the needle is then positioned in the interior of the port 17. The medical fluid is injected from the syringe into the port 17. As a result, the medical fluid is caused to pass from the interior of the port 17 through the interior of the valved catheter 10, and is subsequently introduced into the superior caval vein B2 through the slit 14. When the pressure exerted on the medical fluid from the syringe is greater than the pressure of the blood within the superior caval vein B2, the edge portions 15, 16 of the valve 13 deform outwardly from the valved catheter 10 and the slit 14 opens. In this case, the slit 14 is initially caused to open due to the deformation of the edge portion 16 outward, whereupon the edge portion 15 is then deformed, and the slit 14 is caused to open further, due to the force that is subsequently generated by the flow of the medical fluid.

Moreover, processes pertaining to blood extraction and confirmation of blood reflux include the needle of the syringe in a vacuum state being inserted through the surface of the skin and passed through the septum 19. When the tip of the syringe is positioned in the interior of the port 17, the plunger of the syringe is pulled. As a result, the blood in the vein passes from the superior caval vein B2 through the slit 14 into the interior of the valved catheter 10. At this time, the slit 14 is caused to open toward the interior of the valved catheter 10 as a result of deformation of the edge portions 15, 16 of the valve 13 generated by the suction force of the syringe. In this case, the slit 14 is caused to open initially due to inward deformation of the edge portion 15, and the edge portion 16 then deforms, and the slit 14 is caused to open further, due to the force subsequently generated by the flow of the medical fluid. At this time, the edge portion 16 deforms outward.

Accordingly, when a medical fluid is delivered through the valved catheter 10 into a vein or when blood from a vein is suctioned into the interior of the valved catheter 10, the slit 14 is able to open readily and the medical fluid or blood is able to flow smoothly therethrough. In addition, when the pressure of the medical fluid or blood drops, the slit 14 does not close immediately and instead closes gradually in accordance with the drop in pressure. Furthermore, when no medical fluid is being injected and no blood is being suctioned using the syringe, the closed state of the slit 14 is maintained due to the restoring force of the valve 13 afforded by the resilience thereof.

In the valved catheter 10 pertaining to this embodiment which includes the valve 13 constituted by the slit 14 and the edge portions 15, 16 located at the two sides of the slit 14 in this way, the slit 14 is formed in a linear shape in position away from the center line "c" of the valved catheter 10 in such a way as to extend in parallel with the center line "c." Accordingly, when a medical fluid is delivered from the valved catheter 10 into the vein, the edge portion 16 deforms more readily than the edge portion 15 and, when the blood of a vein is suctioned into the interior of the valved catheter 10, the edge portion 15 deforms more readily than the edge portion 16. As a result, the edge portions 15, 16 do not open simultaneously and, instead, the slit 14 opens slightly due to the initial deformation of either the edge portion 16 or the edge portion 15, and the slit 14 then opens sufficiently to allow the medical fluid or blood to pass therethrough when the force generated by the flow of medical fluid or blood is subsequently exerted thereon.

In addition, once the slit 14 is open, because the slit 14 does not close until the fluid pressure drops and either the more readily deforming edge portion 16 approaches the other edge portion 15 or the more readily deforming edge portion 15 approaches the other edge portion 16, the slit 14 closes gradually and the rapid closure thereof is prevented. Accordingly, the slit 14 opens readily not only when a medical fluid flows from the interior to the exterior of the valved catheter 10 but also when blood flows from the exterior to the interior thereof, and a smooth interior/exterior bi-directional flow of medical fluid or blood is afforded thereby. In addition, because the distance "a" from the center line "c" to the slit 14 is longer than the distance "b" from the tangent line "d" to the slit 14, the production of an ideal slit 14 in terms of both the suitability of the ease of opening thereof and being able to close gradually in response to the drop in fluid pressure when closing from an opened state is afforded thereby.

Figures 4A, 4B:
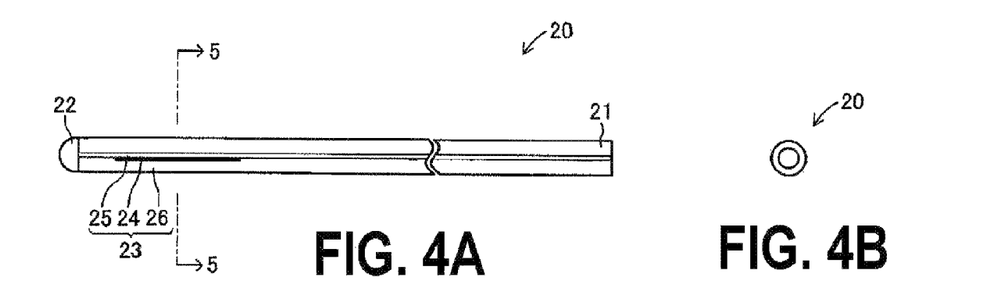
FIG. 4A is a side view and FIG. 4B is a rear view thereof.
Figure 5:
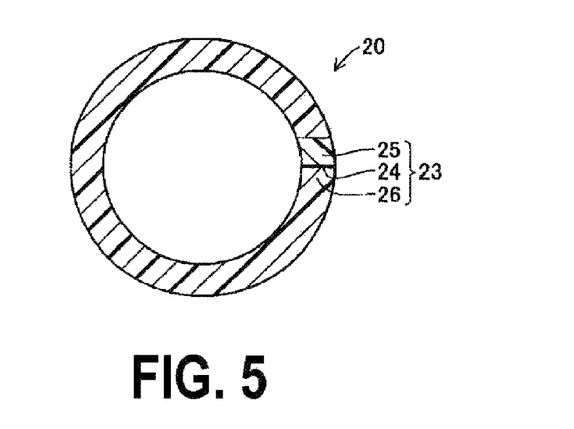
FIG. 5 is a cross-sectional view taken along the line 5-5 of FIG. 4A.

FIG. 4 and FIG. 5 show a valved catheter 20 pertaining to a second embodiment of the present disclosure. Similarly to the valved catheter 10 described above, the valved catheter 20 has an open proximal end portion 21 and a dome-shaped wall portion 22 formed in its distal end. A valve 23 of this embodiment is constituted by a linear slit 24 provided to extend in the axial direction of the valved catheter 20, and by edge portions 25, 26 formed in the two sides of the slit 24 in the circumferential direction. The slit 24 is formed in such a way as to lie on an imaginary straight line (not shown in the drawing) passing through a center point in the cross-section of the valved catheter 20 shown in FIG. 5.

In addition, while the resin material from which the edge portion 25 is constituted is a polyurethane of the same type as the other sections from which the valved catheter 20 is constituted, this polyurethane is softer than the polyurethane from which the other sections are constituted, and the sections composed of this soft resin material include the edge portion 25 section adjacent to the slit 24 and sections that extend along the front side and rear side of the edge portion 25. That is to say, the edge portion 25 is constituted from a soft section in the section that extends from the proximal end to the distal end section of the valved catheter 10 excluding the wall portion 22, and the section thereof adjacent to the slit 24. The constitution of the other sections of the valved catheter 20 is identical to the constitution of the other sections of the valved catheter 10 of the first embodiment described above.

The operations performed employing the valved catheter 20 to deliver a medical fluid into the vein of a patient A or to suction blood from a vein are identical to the operations performed employing the valved catheter 10 as described above to deliver a medical fluid into the vein of a patient A or suctioning blood from a vein. Accordingly, when either a medical fluid is caused to flow from the interior to the exterior of the valved catheter 20 or when blood is caused to flow from the exterior to the interior thereof, the edge portion 25 responds more sensitively to changes in fluid pressure than the edge portion 26 and, in turn, deforms more readily than the latter. The remaining action and effects of the valved catheter 20 are identical to the action and effects afforded by the valved catheter 10.

Figure 6A:
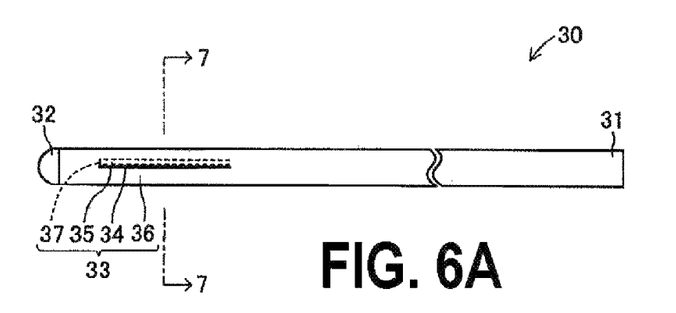
FIG. 6A is a side view and FIG. 6B is a rear view thereof.
Figure 6B:
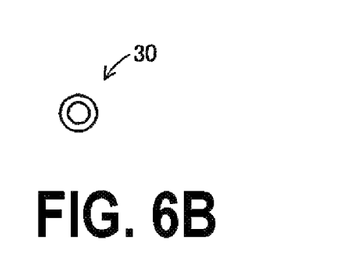
Figure 7:
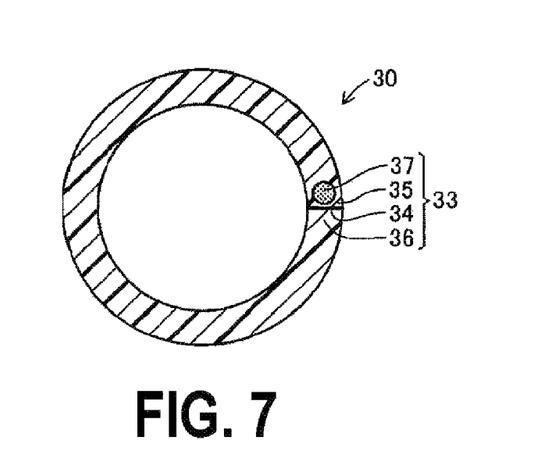
FIG. 7 is a cross-sectional view taken along the line 7-7 of FIG. 6A.

FIG. 6 and FIG. 7 show a valved catheter 30 pertaining to a third embodiment of the present disclosure. Similarly to the valved catheter 10, the valved catheter 30 includes an open proximal end portion 31 and has a dome-shaped wall portion 32 formed in its distal end. A valve 33 thereof is constituted by a linear slit 34 provided to extend in the axial direction of the valved catheter 30, edge portions 35, 36 formed in the two sides of the slit 34 in the circumferential direction, and a contrast-imparted portion 37 formed in the interior of the edge portion 35. The slit 34 is formed in such a way as to lie on an imaginary straight line (not shown in the drawing) passing through a center point in the cross-section of the valved catheter 30 shown in FIG. 7.

In addition, the contrast-imparted portion 37, which is constituted by admixing a polyurethane resin with a contrast-imparting material composed of a barium or tungsten powder or the like of greater hardness than the polyurethane resin, is formed in parallel with the slit 34 in a section adjacent to the slit 34. The contrast-imparted portion 37 prevents the transmission of X-rays therethrough and, accordingly, when irradiated with X-rays, a shadow is formed and a contrast with the other sections is created thereby. This contrast affords confirmation of the position of the distal end section of the valved catheter 30 when it is placed in the body. The constitution of the other sections of the valved catheter 30 is identical to the constitution of the valved catheter 10 of the first embodiment described above.

The operations performed employing the valved catheter 30 to deliver a medical fluid into the vein of a patient A or to suction blood from a vein are identical to the operations performed employing the valved catheter 10 as described above to deliver a medical fluid into the vein of a patient A or to suction blood from a vein. Accordingly, because the edge portion 35 is made less readily deformable than the edge portion 36 by the provision of the contrast-imparted portion 37, when either a medical fluid is caused to flow from the interior to the exterior of the valved catheter 30 or when blood is caused to flow from the exterior to the interior thereof, the edge portion 36 responds more sensitively to changes in fluid pressure than the edge portion 35 and, in turn, deforms more readily than the latter. Furthermore, a contrast is produced between the contrast-imparted portion 37 and the other sections when they are irradiated with X-rays, and therefore it is possible to confirm the position of the distal end section of the valved catheter 30 inside the body. The remaining action and effects of the valved catheter 30 are identical to the action and effects of the valved catheter 10.

Figure 8:
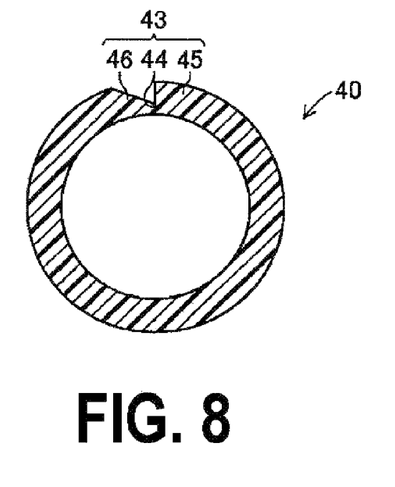
FIG. 8 is a cross-sectional view of a distal end section of a valved catheter of a fourth embodiment of the present disclosure.

FIG. 8 shows a cross-section of the distal end section of the valved catheter 40 pertaining to a fourth embodiment of the present disclosure. The valve 43 of this valved catheter 40 is constituted by a linear slit 44 provided to extend along the axial direction (the direction orthogonal to the plane of the paper of FIG. 8) of the valved catheter 40, and by edge portions 45, 46 formed in the two sides of the circumferential direction of the slit 44. The edge portion 46 is formed thinner than the edge portion 45 due to the formation of an inclined face in the outer circumferential side of a section adjacent to the slit 44 of the valved catheter 40 that thins gradually toward the slit 44 side. While there is no hard section and no contrast-imparted portion provided in the valved catheter 40, the constitution of the other sections of the valved catheter 40 is identical to the constitution of the valved catheters 20, 30 described above.

The operations performed employing the valved catheter 40 to deliver a medical fluid into the vein of a patient A or to suction blood from a vein are identical to the operations performed when employing the valved catheter 10 as described above to deliver a medical fluid into the vein of a patient A or to suction blood from a vein. Accordingly, the edge portion 46 is formed thinner than the edge portion 45 and, as a result, deforms more readily than the latter. As a result, when either a medical fluid flows from the interior to the exterior of the valved catheter 40 or when blood flows from the exterior to the interior thereof, the edge portion 46 deforms prior to the edge portion 45 and the slit 44 opens readily. The other action and effects of the valved catheter 40 are identical to the action and effects of the valved catheter 10 described above.

Figure 9:
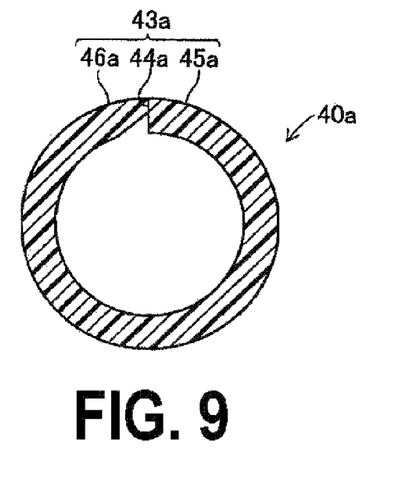
FIG. 9 is a cross-sectional view of a distal end section of a valved catheter of a modified example of the fourth embodiment.

FIG. 9 shows a cross-section of a distal end section of a valved catheter 40a pertaining to a modified example of the fourth embodiment of the present disclosure. A valve 43a of this valved catheter 40a is constituted by a linear slit 44a provided to extend along the axial direction of the valved catheter 40a, and by edge portions 45a, 46a formed in the two sides of the circumferential direction of the slit 44a. The edge portion 46a is formed thinner than the edge portion 45a due to the formation of an inclined face in the outer circumferential side of a section adjacent to the slit 44a of the valved catheter 40a that thins gradually to the slit 44a side. The constitution of the other sections of the valved catheter 40a is identical to the other sections of the valved catheters 40 described above.

The operations performed employing the catheter 40a to deliver a medical fluid into the vein of a patient A or to suction blood from a vein are identical to the operations performed employing the valved catheter 10 as described above to deliver a medical fluid into the vein of a patient A or to suction blood from a vein. The other action and effects afforded by the valved catheter 40a are identical to the actions and effects of the valved catheter 40 described above.

Figure 10:
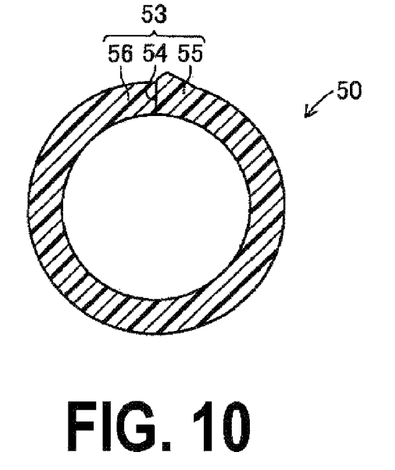
FIG. 10 is a cross-sectional view of a distal end section of a valved catheter of a fifth embodiment of the present disclosure.

FIG. 10 shows a cross-section of a distal end section of the valved catheter 50 of a fifth embodiment of the present disclosure. The valve 53 of this valved catheter 50 is constituted by a linear slit 54 provided to extend along the axial direction of the valved catheter 50, and by edge portions 55, 56 formed in the two sides of the circumferential direction of the slit 54. The edge portion 55 is formed thicker than the edge portion 56 due to the formation of a projecting portion in the outer circumferential side of a section adjacent to the slit 54 of the valved catheter 50. The constitution of the other sections of the valved catheter 50 is identical to the other sections of the valved catheters 40 described above.

The operations performed employing the valved catheter 50 to deliver a medical fluid into the vein of a patient A or to suction blood from a vein are identical to the actions performed employing the valved catheter 10 as described above to deliver a medical fluid into the vein of a patient A or to suction blood from a vein. Accordingly, the edge portion 55 is formed thicker than the edge portion 56 and, as a result, deforms less readily than the latter. As a result, when either a medical fluid flows from the interior to the exterior of the valved catheter 50 or when blood flows from the exterior to the interior thereof, the edge portion 56 deforms prior to the edge portion 55 and the slit 54 opens readily. The other action and effects of the valved catheter 50 are identical to the action and effects of the valved catheter 40 described above.

Figure 11:
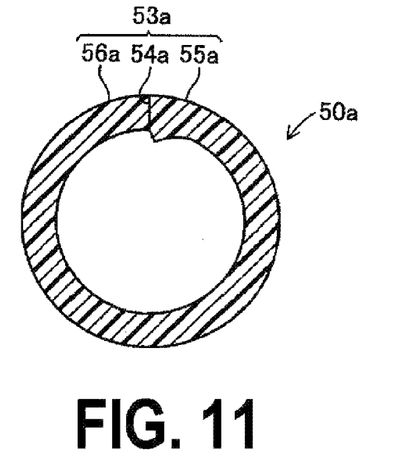
FIG. 11 is a cross-sectional view of a distal end section of a valved catheter of a modified example of the fifth embodiment.

FIG. 11 shows a cross-section of a distal end section of the valved catheter 50a pertaining to a modified example of the fifth embodiment of the present disclosure. The valve 53a of this valved catheter 50a is constituted by a linear slit 54a provided to extend along the axial direction of the valved catheter 50a, and by edge portions 55a, 56a formed in the two sides of the circumferential direction of the slit 54a. The edge portion 55a is formed thicker than the edge portion 56a due to the formation of a projecting portion in the outer circumferential side of a section adjacent to the slit 54a of the valved catheter 50a. The constitution of the other sections of the valved catheter 50a is identical to the other sections of the valved catheter 50 described above.

The operations performed employing this valved catheter 50a to deliver a medical fluid into the vein of a patient A or to suction blood from a vein are identical to the operations performed when employing the valved catheter 10 as described above to deliver a medical fluid into the vein of a patient A or to suction blood from a vein. The other action and effects afforded by the valved catheter 50a are identical to the action and effects afforded by the valved catheter 50 described above.

In addition, it should be understood that the valved catheter pertaining to the present disclosure is not limited to the embodiments described above, and that various alterations may be made thereto. For example, while the embodiments described above describe the employment of a polyurethane as the resin from which the valved catheter 10 and so on is constituted, in addition to polyurethane, silicon, nylon or polyvinylchloride or the like may also be employed. In addition, while the sections of the valved catheter 20 of the second embodiment described above which are composed of a hard resin material include the edge portion 25 and the section formed along the proximal and distal ends of the edge portion 25, only the edge portion 25 need be formed as a hard section. In this case, the main body of the valved catheter 20 is constituted from three sections, that is to say, a section in which the slit 24 and the edge portion 25 are formed, and sections to the proximal side and to the distal side thereof, and these sections are connected by adhesion or fusion.

In addition, while the third embodiment described above describes the provision of the valved catheter 30 including the contrast-imparted portion 37 in the section adjacent to the slit 34 only, the contrast-imparted portion 37 may be formed to extend from the proximal end to the distal end of the section of the valved catheter 30 excluding the wall portion 32. That is to say, it may be linearly formed from the proximal end to the distal end of the main body of the valved catheter 30. This simplifies the manufacture of the valved catheter 30. Furthermore, while the embodiments described above describe the connection of the port 17 to the proximal end portion 11 of the valved catheter 10 and so on, the proximal end portion 11 of the valved catheter 10 and so on may be connected to a transfusion line. In addition, while the embodiments described above describe the placement of the valved catheter 10 and so on in a vein, the valved catheter 10 and so on may be placed in an artery in accordance with a predetermined method.

Furthermore, while the embodiments described above describe the valved catheter 10 and so on as having a circular cross-sectional shape, the cross-sectional shape of the valved catheter 20 and so on of the second to fifth embodiments of the valved catheter 20 and so on is not limited to a circular shape, and they may be either elliptical in shape, or another shape such as a square shape with curved corners, or another polygonal shape. In addition, while ensuring the appropriate combination of constituent sections of the valved catheter 10 and so on including the shape of the slit 14 and so on, the shape of the edge portion 15 and so on and the contrast-imparted portion 37, the provision of a plurality thereof with respect to a single valved catheter is also possible. It is sufficient, as a result, for a first edge portion to be able to be deformed more readily than another edge portion.

What is claimed is:

1. A resilient and flexible valved catheter which is made from a resin and which includes a tubular body having a closed distal end, the valved catheter having a valve comprising an openable slit that penetrates from an inner surface to an outer surface of the body, the slit extending in a longitudinal direction along the body in a distal end section of the valved catheter, the openable slit including two sides each having an edge portion, wherein a first one of the edge portions moves more readily than a second one of the edge portions in an outward direction when fluid is caused to flow from an interior to an exterior of the valved catheter by way of the valve, and wherein the second one of the edge portions moves more readily than the first one of the edge portions in an inward direction when fluid is caused to flow from the exterior to the interior of the valved catheter by way of the valve, wherein a thickness of one edge portion of the slit of the valve is thinner than the other edge portion.

2. The valved catheter according to claim 1, wherein adjoining sections of the edge portions of the slit include a shape in cross-section orthogonal to the longitudinal direction of the distal end of the valved catheter which is asymmetrical about the slit.

3. The valved catheter according to claim 1, wherein the tubular body of the valved catheter includes a circular cross-section and the slit includes a linear shape in cross-section in a position away from an imaginary straight line that passes through a center of the valved catheter and extends in parallel with the imaginary straight line and, taking a minimum distance from the imaginary straight line to the slit as "a," and a distance equivalent to "a" subtracted from ½ of an inner diameter of the circular tube-shaped body as "b," "a" is larger than "b."

4. The valved catheter according to claim 1, wherein each edge portion pivots in the same clockwise or counterclockwise direction as the other edge portion to open the openable slit.

5. A catheter, comprising:
a tubular body having a closed distal end and defining a valve in a distal end section of the tubular body, the valve including a pair of edge portions that define a slit, the slit extending longitudinally along the tubular body and extending between an inner surface of the tubular body and an outer surface of the tubular body, wherein one of the edge portions includes a contrast-imparting portion formed of a contrast-imparting material, wherein the contrast imparting portion is composed of a polyurethane resin and a contrast-imparting material, the contrast-imparting material having a hardness greater than the hardness of the polyurethane resin.

6. The catheter according to claim 5, wherein the contrast-imparting material is disposed on an interior portion of the tubular body.

7. The catheter according to claim 5, wherein the contrast-imparting portion is parallel to the slit.

* * * * *